(12) United States Patent
Klein et al.

(10) Patent No.: US 7,666,218 B2
(45) Date of Patent: Feb. 23, 2010

(54) DEVICE FOR THE APPLICATION OF COMPRESSION SLEEVES

(75) Inventors: Marco Klein, Zwickau (DE); Christian Staier, Sinsheim (DE); Bernd Vogel, Karlsruhe (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 313 days.

(21) Appl. No.: 11/728,583

(22) Filed: Mar. 26, 2007

(65) Prior Publication Data

US 2007/0225793 A1    Sep. 27, 2007

Related U.S. Application Data

(63) Continuation-in-part of application No. PCT/EP2005/010250, filed on Sep. 22, 2005.

(30) Foreign Application Priority Data

Sep. 27, 2004    (DE) .................. 10 2004 046 840

(51) Int. Cl.
*A61F 2/06*    (2006.01)

(52) U.S. Cl. ....................... 623/1.11; 606/108
(58) Field of Classification Search ............ None
See application file for complete search history.

(56) References Cited

U.S. PATENT DOCUMENTS

| | | | |
|---|---|---|---|
| 5,211,649 A | | 5/1993 | Kohler et al. |
| 5,972,003 A | * | 10/1999 | Rousseau et al. ............ 606/142 |
| 6,648,911 B1 | | 11/2003 | Sirhan et al. |
| 2002/0022837 A1 | * | 2/2002 | Mazzocchi et al. ............ 606/41 |

* cited by examiner

*Primary Examiner*—Todd E Manahan
*Assistant Examiner*—Brian Graham
(74) *Attorney, Agent, or Firm*—Klaus J. Bach

(57) ABSTRACT

In a device for the installation of a compression sleeve around a blood vessel, including a guide element for holding the blood vessel, and a carrier for holding the compression sleeve in a bent-open state in which the carrier and the compression sleeve are supported at the distal end of the installation device, the installation device includes a push element for pushing the compression sleeve off the carrier while the blood vessel is disposed in the bent-open compression sleeve so that, upon its release from the carrier, the compression sleeve extends tightly around the blood vessel.

6 Claims, 2 Drawing Sheets

DEVICE FOR THE APPLICATION OF COMPRESSION SLEEVES

This is a Continuation-In-Part Application of pending International Patent Application PCT/EP2005/010250 filed Sep. 22, 2005 and claiming the priority of German Patent Application 10 2004 04 68 40.0 filed Sep. 22, 2004.

BACKGROUND OF INVENTION

The invention relates to an installation device for compression sleeves of the type as disclosed in principle in DE 103 55 986 for the local enclosure of a blood vessel for example for supporting a body internal vein valve, including a guide structure for the blood vessel and means for applying the compression sleeve.

Weak tissue areas in the human body, particularly of blood vessels lead with increasing age to significant vessel expansions. This effect becomes particularly pronounced if the vein valve systems in the blood circuit have been expanded to such an extent that they don't function any more as unidirectional valves (check valves or one way valves) so that reflux occurs and the individual blood vessels are subjected to additional fluid pressure stresses.

Without treatment, this effect results in a massive formation of varicose veins, particularly in the legs of a person. This formation begins first with a vessel expansion particularly in weak or resilient tissue areas such as the vein walls. Later also the vein valves also for example in the pelvic area may expand and, in time, generally fail. Finally, enhanced by gravity, a blood backup and pressure stresses occur resulting in further expansions in the veins of the legs. The expansion of the veins (dilatations) results first in varicose veins and later in open wounds on the legs.

For an effective or preventative treatment of varicose veins, a maintenance or restitution of functional veins and vein valves is very important. Ideally the dilation of veins or vein valves should be counteracted early preferably by a reinforcement of the tissue.

U.S. Pat. No. 5,500,014 discloses several embodiments of a support sleeve for blood vessels all of which have a tubular form. Consequently, the blood vessel must be inserted through the sleeve for which purpose it needs to be cut. Also, the support sleeves are not designed for a fast over growth by the tissue.

As described in DE 103 55 986 this disadvantage can be avoided by the use of an improved compression sleeve which consists essentially of an elastically bendable mat of a biocompatible material (for example, titanium, nickel-titanium alloys). With this mat, a blood vessel is enveloped in a locally delimited area, preferably in the area of weakened vein tissue or of a vein valve. The blood vessel no longer needs to be cut in the procedure. In a particular embodiment, a super-elastic pretension of the mat is sufficient for reliably containing a blood vessel.

Based hereon, it is the object of the present invention to provide a device for the application of such a super-elastic compression sleeve which permits surgical operation for the installation of such a mat in a relatively unobjectionable manner.

SUMMARY OF THE INVENTION

In a device for the installation of a compression sleeve around a blood vessel, including a guide element for holding the blood vessel, and a carrier for holding the compression sleeve in a bent-open state in which the carrier and the compression sleeve are supported at the distal end of the installation device, the installation device includes a push element for pushing the compression sleeve off the carrier while the blood vessel is disposed in the bent-open compression sleeve so that, upon its release from the carrier, the compression sleeve extends tightly around the blood vessel.

The super-elastic mat encloses the vein when it is pushed off the carrier structure on which it is supported in the bent-open form and elastically abuts the wall of the blood vessel. The elastic mat is pushed off the carrier structure by a slide element. The slide-ff direction may be axial or radial with respect to the extension of the compression sleeve on the carrier, wherein an axial sliding off of the bent-open compression sleeve onto a vein occurs preferably at an acute angle relative to the vein.

To this end, the application device comprises an end piece for surrounding or fixing the blood vessel during the operation in the form of, for example, a longitudinally slotted tube section which is open at both ends or a U-shaped bent metal sheet as well as a carrier for an elastically bent-open U-flank into the tubular section and is aligned relative to the carrier.

The guide structure should permit the blood vessel to yield to possible load stresses during the slide-on procedure, that is, the blood vessel should be rotatable or axially slidable within the guide structure. The tube section is preferably straight or slightly curved so that the blood vessel is axially slidable or rotatable about the axis of the tube section within the tube section without substantial resistance.

At the proximal actuating end, the guide structure is provided with a guide element extending axially from the guide structure, whereby the guide structure can be positioned within a patient's body during installation of the compression sleeve. Furthermore, the installation device comprises a slide element for remotely pushing the component off the installation device, that is the guide structure, over the blood vessel.

The end piece is preferably V-shaped, that is, the guide structure and the tube section form flanks which join at the distal end of the V-shaped end pieces. They extend at the proximal end at an acute angle relative to each other and penetrate each other at the distal end where they are joined. The tube section remains preferably unchanged in its cylindrical internal dimensions. Herein, the open tube section end is positioned within the converging area in the end cross-section of the carrier. The carrier may have a larger cross-section than the tube section so that, during the pushing off of the compression sleeve, a further temporary widening of the compression sleeve by the tube section is avoided in the penetration area or is at least limited geometrically. In this procedure, the compression sleeve is shortly additionally widened in the area where the tube section joins the carrier at an acute angle α and is pushed onto the blood vessel.

The invention will become more readily apparent from the following description of an embodiment thereof with reference to the accompanying drawings.

DESCRIPTION OF THE VARIOUS EMBODIMENTS

Figure 1:
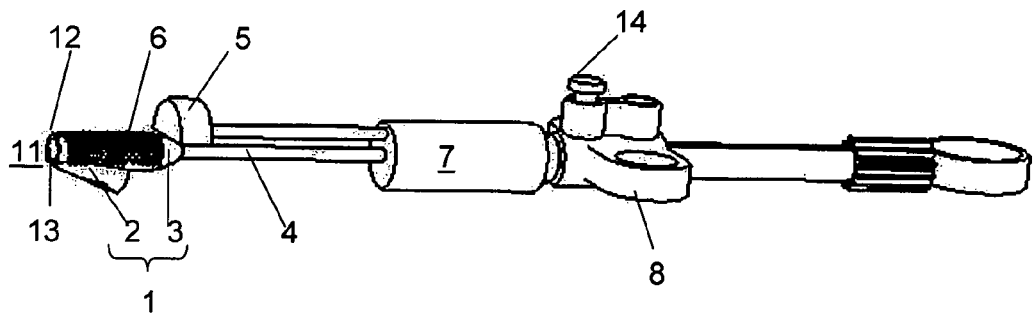
FIG. 1 shows a first embodiment of an application device including a carrier with a cylindrical compression sleeve disposed thereon.

The first two embodiments (FIGS. 1 to 4) comprise essentially the V-shaped end piece 1 consisting of a tube section 2 and a carrier 3, a guide element 4 and a push member 5 for pushing a preferably, cylindrical compression sleeve 6 as described for example in DE 103 55 986 disposed on the carrier 3 off the distal end of the device. The embodiment shown furthermore comprises a guide block 7 for parallel guidance and a handle 8 with a mechanism for moving the guide element 4 and the push element 5 in opposite directions. In the perspective view of the second embodiment according to FIG. 4, the guide element 4 is invisible in the area of the push element 5.

Figure 4:
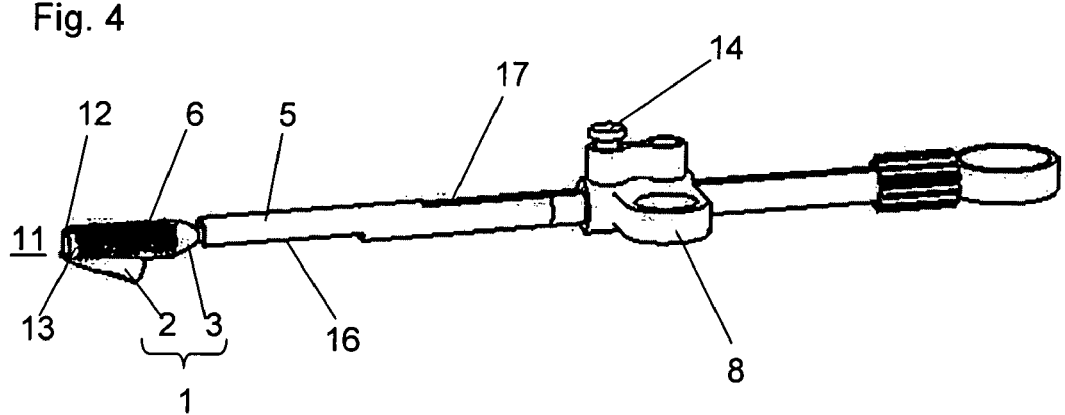
FIG. 4 shows a second embodiment of the application device with a slightly different dilating element.

During the movement in opposite directions as mentioned above the guide element or the push element may be fixed by suitable means which, as shown in FIGS. 1 and 4, may be a rotatable button. A compression sleeve is pushed off the device and onto a blood vessel in a particularly gentle way if the compression sleeve does not move relative to the blood vessel, that is, if the end piece is at the same time pulled out axially from under the compression sleeve while the compression sleeve is held in position by the push member so that the compression sleeve is simply deposited onto the blood vessel without relative axial movement therebetween.

Figure 2:
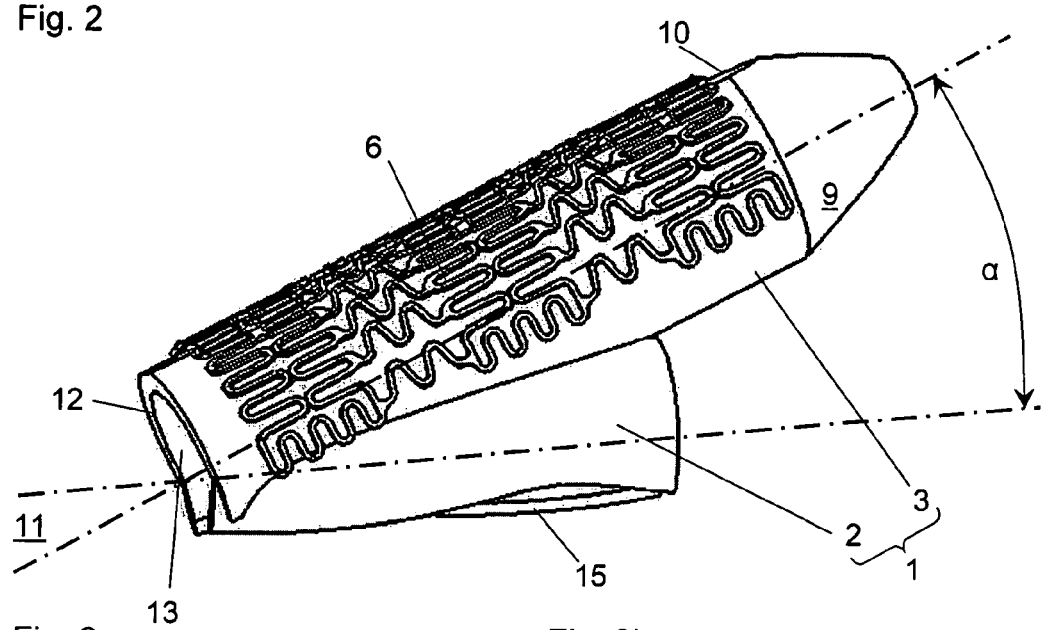
FIG. 2 shows the end piece of the device shown in FIG. 1 with the compression sleeve disposed therein.
Figure 3A:
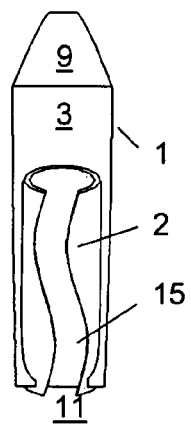
FIGS. 3a and 3b show the end piece of FIG. 2 in two different views.

The push element 5 of the first embodiment is disposed in the form of a compact component on a push rod and engages the compression sleeve being pushed off only at a point in the upper area above the groove 10 (FIG. 2 and 3a). The groove 10 guides the component mentioned above and particularly, prevents the component from sliding off the front side onto the surface of the compression sleeve of the carrier. This security effect can be enhanced by structures on the front side of the push element.

In a second embodiment, the push element (FIG. 4) is in the form of a tube which, guided at the distal end by the carrier, is in contact with a large area of the compression sleeve front side. The sliding off mentioned earlier (first embodiment) is prevented by providing for little play between the inner tube surface and the carrier. A groove as provided in the embodiment described earlier is not absolutely necessary.

This more compact design of the push element in accordance with the second embodiment however has some limitation in that, in unmodified form, it cannot be moved over the interference area between the tube section and the carrier. To this end, the tubular push element may be radially expandable, that is, it may be provided with one or more slots, wherein, alternatively, or in addition, the areas which, upon expansion, are particularly deformed are designed so as to be resiliently deformable for example by a targeted low material rigidity or by the use of an elastomer. FIG. 4 for example, discloses a push element 5 in the form of a tube which at the distal end has a wide cutout. It also includes a guide groove 17 forming an additional guide structure in the handle piece for example, via a pin end, which is connected to the rotary knob 14.

Figure 3B:
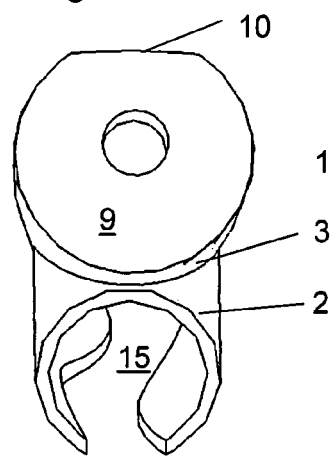

The end piece of the first embodiment is shown in detail in FIGS. 2, 3a, and 3b.

FIG. 2 shows in particular the V-shape of the end piece as well as the jointure of the carrier 3 and the tube section 2.

FIGS. 3a and 3b show the end piece from the bottom and respectively, from the proximal side, wherein the longitudinal slot 15 formed in the tube section is easily recognizable. Through the longitudinal slot, the blood vessel is inserted before the application of the sleeve. Preferably, the longitudinal slot is waved along its length over the tube section and parts of the longitudinal slot are inclined relative to the axis of the tube section. The carrier has the shape of a cylinder below the pried open compression sleeve 6 and has a conical area 9 at its proximal end for facilitating the application of compression sleeve (axial sliding) onto the carrier. Preferably, on the top side of the cylinder-like area of the carrier 3, there is additionally a groove 10 for better guidance on the carrier 3 of the push element 5 shown in FIG. 1. Furthermore, in the distal area 11, the end section 12 of the carrier covers the distal end opening cross-section 13 of the tube section. During an application, that is, when the sleeve is pushed off the carrier, the blood vessel is advantageous disposed completely within the compression sleeve and the elastic pretension cause engagement of the compression sheet with the blood vessel whereupon the application procedure is terminated. The angle $\alpha$ of the V-shaped end is preferably between 20 and 30°. The compression sleeve and the V-shaped end piece are then disposed at an angle of $\alpha=20°$ to 30° with respect to each other, that is the compression sleeve then extends at an angle of $\alpha=20$ to 30° with respect to blood vessel in the tube section.

The end piece of the second embodiment is essentially the same as that shown in FIGS. 2, 3a and 3b, wherein, however, for the reasons mentioned above, the groove 10 may be omitted.

A cylinder-shaped compression sleeve with a diameter of about 5 mm may be pushed onto the carrier 3 via the conical end thereof, whereby the compression sleeve is expanded for example to a diameter of about 10 mm.

The application device may also comprise two parts wherein one part is in the form of a one way component comprising the end piece preferably with a compression sleeve already disposed thereon by the manufacturer and another component which is reusable and includes the handle part. Certain parts, for example the guide block, the guide element and/or the push element may be part of either the one-way component or the reusable component-depending on the particular design.

Figure 5:
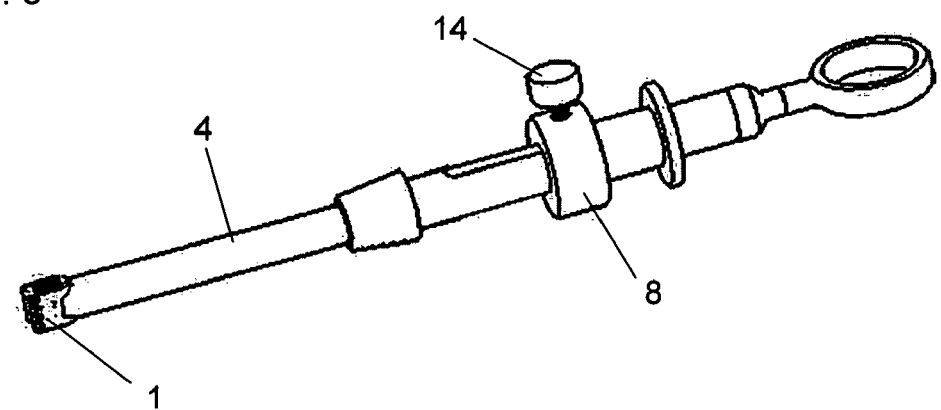
FIG. 5 shows a third embodiment with an end piece including a U-shaped metal strip.
Figure 6A:
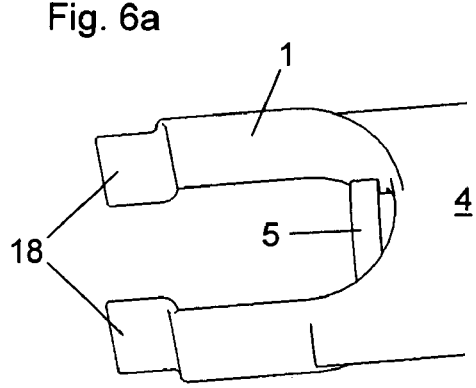
FIGS. 6a and 6b show the end piece of a third embodiment comprising a U-shaped metal strip without, and with, a compression sleeve supported therein.
Figure 6B:
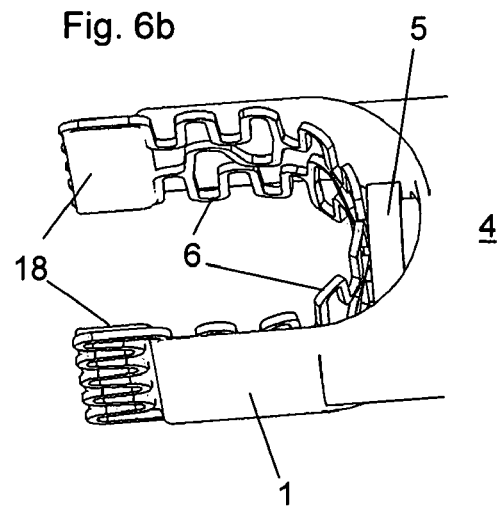

A third embodiment is shown in FIGS. 5, 6a and 6b. As in the first two embodiments, the application device comprises also in this case a handle 8 with a rotary bottom 14 for locking the push element. As guide element 4, a tube is provided, at the distal end of which the end piece 1 is disposed. The end piece comprises essentially a U-shaped bent material strip for guiding the blood vessel and for supporting the compression sleeve 6 (see FIG. 6b). In the guide element 4, the push element 5 is axially guided (see FIGS. 6a and 6b), wherein the distal end of the push element extends between the two flanks 18 of the U-shaped bent metal strip into the interior of the U-shaped bent metal strip. With the movement of the guide element 4 and the push element 5 in opposite directions, the push element can be moved toward the distal end whereby it engages centrally the compression sleeve 6 held by the two flanks 18 and pushes the sleeve forward and off the end piece over the blood vessel which extends in this case normal to the longitudinal axis of the application device.

What is claimed is:

1. A device for the installation of a compression sleeve (6) around a blood vessel, comprising:

a) a guide element (4) for holding the blood vessel, said guide element (4) consisting of a tube section (2) which is open at both ends and provided with a longitudinal slot (15) for receiving the blood vessel;

b) a carrier (3) for holding the compression sleeve (6) in a bent-open state, the guide element (4) and the carrier (3) forming together a V-shaped end piece (1), the carrier 3 and the tube section forming the flanks of the V-shaped end piece (1) with an acute angle (α) at the distal end of the end piece and c) a push element (5) for pushing the compression sleeve (6) off the carrier (3) while the blood vessel is contained in the bent-open compression sleeve (6) so that the blood vessel is engaged in the compression sleeve (6) after its release from the carrier (3).

2. The application device according to claim 1, wherein sections of the longitudinal slot extend skewed with respect to the axis of the tube section.

3. The application device according to claim 1, wherein the carrier (3) includes a cylindrical area for supporting the compression sleeve (6), said cylindrical area having a diameter exceeding that of the tube section (2).

4. The application device according to claim 1, wherein the carrier (3) is provided at its proximal end with a conical end (9) for sliding the compression sleeve (5) onto the carrier (3).

5. The application device according to claim 1, wherein the end piece (1) is part of a one-way installation component.

6. The application device according to claim 5, wherein the one-way installation component includes a compression sleeve (6) already disposed on the carrier (3).

* * * * *